(12) United States Patent
Desjardins et al.

(10) Patent No.: US 7,041,642 B1
(45) Date of Patent: May 9, 2006

(54) FLUORESCENT BOMBESIN-LIKE PEPTIDES

(75) Inventors: Clarissa Desjardins, Montreal (CA);
Jacek Slon-Usakiewicz, Montreal (CA); Katherine J. Bonter, Montreal (CA)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 09/351,057

(22) Filed: Jul. 12, 1999

Related U.S. Application Data

(63) Continuation-in-part of application No. 08/682,810, filed on Jul. 10, 1996, now Pat. No. 6,054,557, which is a continuation-in-part of application No. 08/504,856, filed on Jul. 20, 1995, now abandoned.

(51) Int. Cl.
*A61K 38/00* (2006.01)

(52) U.S. Cl. .................... 514/12; 530/324; 435/7.1

(58) Field of Classification Search .................. 514/12; 530/324; 435/7.1
See application file for complete search history.

(56) References Cited

U.S. PATENT DOCUMENTS

| 4,046,633 A | 9/1977 | Keutel ................. 195/103.5 R |
| 5,248,782 A | 9/1993 | Haugland ..................... 548/110 |
| 5,274,113 A | 12/1993 | Kang et al. .................. 548/405 |
| 5,693,679 A | 12/1997 | Vincent et al. ............. 530/311 |
| 5,760,188 A | 6/1998 | Beaudet et al. ............. 530/402 |

FOREIGN PATENT DOCUMENTS

| DE | 27 02 699 A1 | 12/1977 |
| DE | 3912046 A1 | 3/1990 |
| EP | 0 007 407 | 2/1980 |
| EP | 0 240 914 A2 | 10/1987 |
| EP | 0 333 071 A3 | 11/1988 |
| EP | 0 331 126 A2 | 9/1989 |
| EP | 0 466 565 A1 | 1/1992 |
| EP | 0 606 804 | 7/1994 |
| EP | 0 608 987 | 8/1994 |
| GB | 2 291 708 A | 1/1996 |
| JP | 63051400 | 3/1988 |

(Continued)

OTHER PUBLICATIONS

Fluorescently-labeled gastrin releasing peptide was first introduced as a product by the assignee, Advanced Bioconcept, Ltd., under the trade name Fluo-GRP™ on Nov. 10, 1997.

(Continued)

*Primary Examiner*—Christopher S. F. Low
*Assistant Examiner*—Amy Lewis
(74) *Attorney, Agent, or Firm*—Iandiorio & Teska

(57) ABSTRACT

Light emitting compounds of the formula:

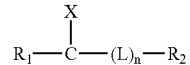

where $R_1$ is a light-emitting moiety, $R_2$ is a bombesin-like peptide and fragment, derivative or analog thereof and L is a linker moiety, which may be present or absent. The peptide is linked at a first amino acid position to (C—X) which, in turn, is selected from the group including C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties. Optionally the compound may include a linker moiety between the peptide and the C—X binding group. Preferably, the compound exhibits substantial biological activity in the presence of receptors having affinities for bombesin-like peptides.

21 Claims, 6 Drawing Sheets

FOREIGN PATENT DOCUMENTS

| WO | WO 93/04194 | 3/1993 |
|---|---|---|
| WO | WO 93/18068 | 9/1993 |
| WO | WO 95/22341 | 8/1995 |
| WO | WO 96/31531 | 10/1996 |
| WO | WO 97/04311 | 2/1997 |

OTHER PUBLICATIONS

Fluorescently-labeled neuromedin-C was first introduced as a product by the assignee, Advanced Bioconcept, Ltd., under the trade name Fluo-NMC™ on Feb. 10, 1998.

Amoscato et al., "Synthesis of Two Biologically Active Fluorescent Probes of Thymopentin" *Peptide Protein Res.*, 29:177-186 (1987).

Ashworth et al., "Visualization of the Thyropoin-releasing Hormone Receptor And Its Ligand During Endocytosis And Recycling" *Proc. Nat'l. Acad. Sci. USA*, 92:512-516 (1995).

Beaudet et al., "Internalization And Intracellular Mobilization Of Neurotensin In Neuronal Cells" *Biochemical Pharmacology*, 47:43-52 (1994).

Beaudet et al., "Annales d'endocrinologie" p. L14, Sep. 1-3, 1994 (conference date).

Bowden et al., "Direct Observation of Substance P-induced Internalization of Neurokinin 1 ($NK_1$) Receptors at Sites of Inflammation" *Proc. Nat'l. Acad. Sci. USA*, 91:8964-8968 (1994).

Bunnett et al., "Characterization Of Receptors Using Cyanine 3-labeled Neuropeptides" *Peptides*, 16:733-740, (1995).

Cardullo et al., "Speract Receptors Are Localized on Sea Urchin Sperm Flagella Using a Fluorescent Peptide Analog" *Developmental Biology*, 162:600-607 (1994).

Carraway et al., "The Isolation of a New Hypotensive Peptide, Neurotensin, From Bovine Hypothalami" *J. of Biological Chemistry*, 248:6854-6861 (1973).

Cauvin et al., "Properties and Distribution of Receptors For Pituitary Adenylate Cyclase Activating Peptide (PACAP) In Rat and Spinal Cord" *Regulatory Peptides*, 35:161-173 (1991).

Chard, *Laboratory Techniques in Biochemistry and Molecular Biology*, Elzevier Biomedical Press, New York.

Cheng et al., "Fluorescent Rhodamine-Labeled Thyroid Hormone Derivatives" *FEBS Letters*, 100:113-116 (1979).

Cheng et al., "Receptor-mediated Uptake Of 3,3'5-triiodo-L-thyronine By Cultured Fibroblasts" *Proc. Nat'l. Acad. Sci. USA*, 77:3425-3429 (1980).

Chersi et al., "Preparation And Utilization Of Fluorescent Synthetic Peptides" *Biochemica et Biophysica Acta*, 1034: 333-336 (1990).

Christophe, "Type I Receptors For PACAP (A Neuropeptide Even More Important Than VIP?)" *Biochimica et Biophysica Acta*, 1154:183-199 (1993).

Cushman, "Spectrophotometric Assay And Properties Of the Angiotensin-converting Enzyme of Rabbit Lung" *Biochemical Pharmacology*, 20:1637-1648 (1971).

Epelbaum, "Somatostatin Receptors In the Central Nervous System" *Basic and Chemical Aspects of Neuroscience*, 4:17-28 (1992).

Faure et al., "Binding and Internalization of Neurotensin In Hybrid Cells Derived From Septal Cholinergic Neurons$^\alpha$" *Annals of the New York Academy of Sciences*, 668:345-347 (1992).

Faure et al., "Synthesis of a Biologically Active Fluorescent Probe For Labeling Neurotensin Receptors" *The Journal of Histochemistry and Cytochemistry*, 42:755-763 (1994).

Garland et al., "Agonist-induced Internalization Of the Substance p ($NK_1$) Receptor Expressed in Epithelia Cells" *Biochem. J.*, 303:177-186 (1994).

Grady et al., "Delineation of the Endocytic Pathway of Substance P and Its Seven-Transmembrane Domains NK1 Receptor" *Molecular Biology of the Cell*, 6:509-524 (1995).

Grady et al., "Direct Observation Of Endocytosis Of Gastrin Releasing Peptide And Its Receptor" *J. of Biol. Chem.*, 270:4603-04611 (1995).

Goldstein et al., "DAKLI: A Multipurpose Ligand With High Affinity And Selectivity For Dynorphin (kappa opioid) Binding Sites" *Proc. Nat'l Acad. Sci.*, 85:7375-7379 (1988).

Guillon et al., "Lateral Mobility of the Phospholipase C-activating Vasopressin $V_1$-type Receptor In A7r5 Smooth Muscle Cells: A Comparison With the Adenylate Cyclase-Coupled $V_2$-receptor" *Peptides*, 13:7-11 (1992).

Haigler et al., "Visualization By Fluorescence of the Binding and Internalization of Epidermal Growth Factor In Human Carcinoma Cells A-431" *Proc Natl Acad Sci USA*, 75:3317-3321 (1978).

Haugland et al., *Noninvasive Techniques In Cell Biology*, Wiley-Liss, Inc. (1990).

Haugland, *Handbook of Fluorescent Probes and Research Chemicals*—$5^{th}$ edition (1992).

Hazum et al., "Cluster Formation of Opiate (enkephalin) Receptors In Neuroblastoma Cells: Differences Between Agonists And Antagonists And Possible Relationships To Biological Functions" *Proc. Nat'l. Acad. Sci.*, 77:3038-3041 (1980).

Hazum et al., "Fluorescent And Photo-affinity Enkephalin Derivatives: Preparation And Interaction With Opiate Receptors" *Biochemical And Biophysical Research Communications*, 88:841-846 (1979).

Jans et al., "Lateral Mobility of the Phospholipase C-activating Vasopressin $V_1$-type Receptor In A7r5 Smooth Muscle Cells: A Comparison With the Adenylate Cyclase-coupled $V_2$-Receptor" *EMBO Journal*, 9:2693-2699, (1990).

Kitabgi et al., (eds), *Annals NY Acad. Sci.*, 668:Table of Contents.

Kohzuki et al., "Localization And Characterization of Endothelin Receptor Binding Sites In the Rat Brain Visualized By *In Vitro* Autoradiography" *Neuroscience*, 42:245-260 (1991).

Maxfield, "Fluorescent Analogs Of Peptides And Hormones" *Methods in Cell Biology*, 29:13-28 (1989).

Melander et al., $^{125}$I-Galanin Binding Sites In the Rat Central Nervous System *Handbook of Chemical Neuroanatomy*, vol. II, Elsevier Publishers (1992).

Merchenthaler et al., "Anatomy And Physiology of Central Galanin-containing Pathways" *Prog. Neurobiol.*, 40:711-769 (1993).

Nawa et al., "Nucleotide Sequences of Cloned cDNAs For Two Types of Bovine Brain Substance P Prescursor" *Nature*, 306:32-36 (1983).

Niedel et al., "Receptor-mediated Internalization of Fluorescent Chemotactic Peptide By Human Neutrophils" *Science*, 205:1412-1414 (1979).

Rivier, et al., "D-Trp$^8$-somatostatin: An Analog Of Somatostatin More Potent Than the Native Molecule" *Biochemical and Biophysical Research Communications*, 65:746-751 (1975).

Roettger, et al., "Insulation Of A G Protein-coupled Receptor On the Plasmalemmal Surface Of the Pancreatic Acinar Cell" *J. Cell Biol.*, 130: 579-590 (1995).

Rubanyi et al., "Endothelins: Molecular Biology, Biochemistry, Pharmacology, Physiology, And Pathophysiology" *Pharmacological Reviews*, 46:325-415 (1994).

Sack et al., "Cell Type-specific Binding of *Ricinus* Lectin To Nurine Cerebellar Cell Surfaces In Vitro" *Cell Tissue Research*, 228:183-204 (1983).

Sadoul et al., "Characterization And Visualization Of Neurotensin Binding To Receptor Sites In Human Brain" *Biochem. and Biophys. Res. Comm.*, 120:206-213 (1984).

Schaffer et al., "Fluorescence-activated Cell Sorting Of Embryonic Mouse and Rat Motoneurons and Their Long-term Survival In Vitro" *J. of Neuroscience*, 7:3088-3104 (1987).

Scicchitano et al., "Distribution Of Somatotatin Receptors On Murine spleen And Peyer's Patch T and B Lymphocytes" *Brain, Behavior, and Immunity*, 1:173-184 (1987).

Shecter et al., "Fluorescent Labeling of Hormone Receptors In Viable Cells: Preparation And Properties Of Highly Fluorescent Derivatives of Epidermal Growth Factor and Insulin" *Proc. Nat'l. Acad. Sci. USA*, 75:2135-2139 (1978).

Sigma Immuno Chemicals Company, FluoroTag FITC Conjugation Kit (1994).

Song et al., "Mapping Of Angiotensin II Receptor Subtype Heterogeneity In Rat Brain" *Journal of Comparative Neurology*, 316:467-484 (1992).

St. John et al., "Analysis and Isolation of Embryonic Mammalian Neurons By Fluorescence-Activated Cell Sorting" *Journal of Neuroscience*, 6:1492-1512 (1986).

Tanaka et al., "Structure And Functional Expression of the Cloned Rat Neurotensin Receptor" *Neuron*, 4:947-854 (1990).

Taylor and Wang, "Fluorescently Labelled Molecules As Probes of the Structure And Function Of Living Cells" *Nature*, 284:405-410 (1980).

Tota et al., "Characterization of a Fluorescent Substance P Analog" *Biochemistry*, 33:13079-13086 (1994).

Tota et al., "Interaction of [fluorescein-Trp$^{25}$]Glucagon With the Human Glucagon Receptor Expressed In *Drosophila* Schneider 2 Cells" *J. Biol. Chem.*, 270:26466-26472 (1995).

Varga et al., "Association Of Cell Surface Receptors For Melanotropin With the Golgi Region In Mouse Melanoma Cells", *Proc. Nat. Acad. Sci. USA*, 73:559-562 (1976).

Vrontakis et al., "Isolation and Characterization Of A Complementary DNA (Galanin) Clone From Estrogen-induced Pituitary Tumor Messenger RNA" *Journal of Biological Chemistry*, 262:16755-16758 (1987).

Walker et al., "High level Expression Of Human Neuropeptide Y Receptors In Mammalian Cells Infected With A Recombinant Vaccinia Virus" *Molecular and Cellular Endocrinology*, 91:107-112 (1993).

Weil et al., "Table of Contents" *Basic and Clinical Aspects of Neuroscience* 4:VI-IX (1992).

Yamada et al., "Cloning and Functional Characterization of a Family of Human and Mouse Somatostatin Receptors Expressed in Brain, Gastrointestinal Tract, and Kidney" *Proc. Nat. Acad. Sci.*, 89:251-255 (1992).

Yanagisawa et al., "A Novel Potent Vasoconstrictor Peptide Produced By Vascular Endothelial Cells" *Nature*, 332:411-415 (1988).

Zhao, "Attachment Of A Single Fluorescent Label To Peptides For Determination By Capillary Zone Electrophoresis" *Journal of Chromatography*, 608:239-242 (1992).

Zhuo et al., "Localization and Properties of Angiotensin II Receptors In Rat Kidney" *Kidney International*, 44:S40-S46 (1993).

□ fluo-[D-Phe$^6$,B-Ala$^{11}$,Phe$^{13}$,Nle$^{14}$]Bn(6-14); $K_i$ 0.26 nM
▲ [D-Phe$^6$,B-Ala$^{11}$,Phe$^{13}$,Nle$^{14}$]Bn(6-14); $K_i$ 0.17 nM

SEQUENCE LISTING

```
<160> NUMBER OF SEQ ID NOS: 6

<210> SEQ ID NO 1
<211> LENGTH: 14
<212> TYPE: PRT
<213> ORGANISM: Xenopus tropicalis
<220> FEATURE:
<221> NAME/KEY: VARIANT
<222> LOCATION: (1)...(1)
<223> OTHER INFORMATION: Xaa is Glp, pyroglutamic acid.

<400> SEQUENCE: 1

Xaa Gln Arg Leu Gly Asn Gln Trp Ala Val Gly His Leu Met
 1               5                  10

<210> SEQ ID NO 2
<211> LENGTH: 27
<212> TYPE: PRT
<213> ORGANISM: Homo sapiens

<400> SEQUENCE: 2

Val Pro Leu Pro Ala Gly Gly Gly Thr Val Leu Thr Lys Met Tyr Pro
 1               5                  10                  15

Arg Gly Asn His Trp Ala Val Gly His Leu Met
             20                  25

<210> SEQ ID NO 3
<211> LENGTH: 10
<212> TYPE: PRT
<213> ORGANISM: Homo sapiens

<400> SEQUENCE: 3

Gly Asn Leu Trp Ala Thr Gly His Phe Met
 1               5                  10

<210> SEQ ID NO 4
<211> LENGTH: 10
<212> TYPE: PRT
<213> ORGANISM: Sus scrofa

<400> SEQUENCE: 4
```

```
-continued

Gly Asn His Trp Ala Val Gly His Leu Met
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa is D-phenylalanine
<220> FEATURE:
<221> NAME/KEY: VARIANT
<222> LOCATION: (6)...(6)
<223> OTHER INFORMATION: Xaa is beta-alanine
<220> FEATURE:
<221> NAME/KEY: VARIANT
<222> LOCATION: (9)...(9)
<223> OTHER INFORMATION: Xaa is norleucine

<400> SEQUENCE: 5

Xaa Gly Trp Ala Val Xaa His Phe Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<223> OTHER INFORMATION: Xaa is unknown.

<400> SEQUENCE: 6

Trp Ala Xaa Gly His Xaa Met
1               5
```

FLUORESCENT BOMBESIN-LIKE PEPTIDES

CROSS REFERENCE TO RELATED APPLICATIONS

This application is a continuation-in-part application of U.S. Ser. No. 08/682,810 filed Jul. 10, 1996 and entitled "Fluorescent Peptides" issued as U.S. Pat. No. 6,054,557, which is a continuation-in-part application of U.S. Ser. No. 08/504,856, now abandoned, having the same name and filed Jul. 20, 1995, which are hereby incorporated in their entirety by reference.

BACKGROUND OF THE INVENTION

This invention relates to peptide-based compounds having light-emitting moieties. Peptides may be chemically linked with detectable "labels" and used as probes, for example, to monitor peptide, cytokine, drug, and hormone receptors at the cellular level. Typically, the labeled peptide is placed in contact with a tissue or cell culture where it binds to an available receptor. Once bound, the label is detected, allowing properties such as receptor distribution or receptor binding kinetics to be monitored.

Peptides are typically labeled with radioactive elements such as $^{125}$I or $^{3}$H. In this case, emission of high-energy radioactive particles is monitored using standard γ-ray detectors, thereby allowing detection of the label. While detection techniques for $^{125}$I and $^{3}$H are well-known, radioactive compounds by nature have limited half lives, and are often both toxic and expensive. Moreover, current detection technology makes it difficult or impossible to detect radioactive probes in real-time, thereby precluding study of kinetic processes.

Bombesins are a family of peptide neurotransmitters that share a common C-terminal amino acid sequence Trp-Ala-X-Gly-His-X-Met-NH$_2$. Bombesin-like peptides include gastrin releasing protein (GRP) neuromedin B (NMB), neuromedin C (NMC), ranatensin, litorin and phyllolitorin. Bombesin-like peptides are particularly desirable peptides to label and use to monitor cell receptors, as these peptides exhibit multiple biological roles and their receptors are located in a variety of tissues. Specifically, bombesin-like peptides are localized to the brain (being particularly associated with neurons), intestine, lung, adrenal gland, and pituitary. Receptors for bombesin-like peptides include, for example, bombesin 1 receptor (BB1 or NMB receptor), the bombesin 2 receptor (BB2 or GRP receptor), and bombesin 3 receptor (BB3 or orphan bombesin receptor) and the NMB receptor. Binding to a cognate receptor by a bombesin-like peptide stimulates neurotransmitter activity, (e.g., influencing thermoregulation, homeostasis, metabolism, behavior, stimulation of smooth muscle contraction (e.g., of the intestine, uterus, bladder, etc.), and glandular secretion (e.g., pancreas, anterior pituitary, etc.). Peripheral receptor binding is associated with mitogenic activity in lung cells, (including small-cell lung carcinomas), gastrointestinal tract.

There exists the need for peptides that are chemically linked with detectable labels that are easily detected, yet do not decrease the biological activity of the peptide.

SUMMARY OF THE INVENTION

The present invention provides a compound containing a bombesin-like peptide and a light-emitting moiety that is both biologically active and optically detectable. The peptide is chemically attached to the light-emitting moiety at an amino acid position that is not involved in binding to the peptide receptor. In this way, the peptide's affinity for the binding site is not significantly decreased, and the compound retains high biological activity. Furthermore, the compound can be easily detected using standard optical means.

In general, in one aspect, the invention provides a biologically active compound of the formula:

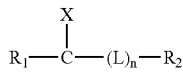

where $R_1$ is a light-emitting moiety, $R_2$ is a bombesin-like peptide and fragment, derivative or analog thereof and L is a linker moiety, which may be present or absent. The peptide is linked at a first amino acid position to (C—X) which, in turn, is selected from the group including C=O, C=S, CH(OH), C=C=O, C=NH, CH$_2$, CH(OR), CH(NR), CH(R), CR$_3$R$_4$, and C(OR$_3$)OR$_4$ where R, R$_3$, and R$_4$ are alkyl moieties or substituted alkyl moieties. Optionally the compound may include a linker moiety between the peptide and the C—X binding group. Preferably, the compound exhibits substantial biological activity in the presence of receptors having affinities for bombesin-like peptides. The compound may also be in the form of a pharmaceutically acceptable salt or complex thereof. Preferably, the N-terminus of said bombesin-like peptide is attached to (C—X), either directly or through a linker moiety.

In preferred embodiments, the bombesin-like peptide can be any peptide that shares sufficient homology with bombesin (SEQ ID NO:1). In particularly preferred embodiments, the bombesin-like peptide is any one of GRP, NMB, or NMC. GRP includes the amino acid sequence Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met (Sequence ID No.2). NMB includes the amino acid sequence Gly-Asn-Leu-Trp-Ala-Thr-Gly-His-Phe-Met (SEQ ID NO:3). NMC includes the amino acid sequence Gly-Asn-His-Trp-Ala-Val-Gly-His-Leu-Met (SEQ ID NO:4). Alternatively, the bombesin-like peptide could be a modified bombesin peptide that includes various substitutions. The peptide [Dphe$^6$, betaAla$^{11}$, Phe$^{13}$, Nel$^{14}$]Bbn(6–14) contains modified amino acids and includes the sequence Dphe-Gly-Trp-Ala-Val-betaAla-His-Phe-Nle (beta Ala represents beta-alanine and Nle represents norleucine) (SEQ ID NO:5). The first residue is attached to the (C—X) moiety and is preferably chemically bound to the (C—X) moiety through the N-terminal amino acid. In still other preferred embodiments, the (C—X) bond is either C=O or C=S. In another preferred embodiment, the peptide may be amidated at the C-terminus. For example, the bombesin like peptides disclosed herein are amidated at the C-terminus.

In other preferred embodiments, the light-emitting moiety ($R_1$) is selected from the group including 4,4-difluoro-4-bora-3a,4a-diaza-s-indacene, fluorescein, fluorsien isothiocyanate (FITC), Texas red, phycoerythrin, rhodamine, carboxytetramethylrhodamine, indopyras dyes, Cascade blue, coumarins, nitrobenzo-2-oxa-diazole (NBD), Lucifer Yellow, propidium iodide, CY3, CY5, CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lys) in the presence of a nucleophile (i.e. CN$^-$) to form fluorescent isoindoles, dansyl dyes fluorescamine and dabcyl chloride, 5-((((2-iodoacetyl)amino)ethyl)amino) naphthalene-1-sulfonic acid, long lifetime dyes comprised of metal-ligand complexes (MLC) which consist of a metal center (Ru, Re, Os) and organic or inorganic ligands complexed to the metal such as such as $[Ru(bpy)_3]^{2+}$ and $[Ru(bpy)_2(dcbpy)]$, and the like and derivatives thereof. The light-emitting moiety can be attached to the peptide by reaction of a reactive side group (of the light-emitting moiety) with the N-terminal amino acid of bombesin-like peptide. Suitable reactive side groups include, by way of example only, indoacetamide, maleimide, isothiocyanate, succinimidyl ester, sulfonyl halide, aldeydes, glyoxal, hydrazine and derivatives thereof.

The above-identified compound is useful in the labeling of cell receptor sites, cell sorting, flow cytometry and performing fluoroimmunoassays. In another aspect, the invention provides a method for labeling a receptor having an affinity for a bombesin-like peptide by contacting the receptor with one or more of the compounds described above. Cell receptor sites, can be imaged by contacting candidate cell receptor sites with the compound of the invention, and then detecting the bound compounds as an indication of the cell receptor sites. Cell sorting can be performed by contacting a population of cells with compound and isolating cells bound to the compound. Flow cytometry can be performed by contacting a population of cells with the compound and detecting cells bearing receptors on their surfaces by detecting cells bound to the compound. In other preferred embodiments it is possible to use the compound to label receptor sites on a model organism, (e.g., *C. elegans*) in order to elucidate the tissue distribution of the receptor sites.

The invention has many advantages. In a general sense, peptide-containing compounds which retain their biological activity after being labeled with light-emitting moieties have a wide variety of biological applications. Such compounds can be used to identify, visualize, quantify, target and select receptors on cells and tissues both in vitro and in vivo. These compounds may be used in place of more conventionally labeled peptides, such a $^{125}I$ radiolabeled peptides. Radiolabeled compounds are often toxic, environmentally hazardous, chemically unstable and have, by the nature of the radioactive decay rate, relatively short lifetimes. In contrast, fluorescently-labeled bombesin-like peptides are relatively safe and non-toxic, thereby allowing it to be synthesized and used without employing special laboratory procedures. Similarly, following use, fluorescent bombesin-like peptides may be easily disposed, whereas disposal of radioactive compounds is both time-consuming and costly. In addition, fluorescent markers for bombesin-like peptide receptors are stable and may be stored for extensive periods of time without undergoing considerable degradation.

Use of bombesin-like peptides in the labeled compound provides several additional advantages. As described above, bombesin-like peptides exhibit biological activity in organs such as the brain, gastrointestinal tract and lung, and are involved in neurotransmitter activity, mitogenic activity and secretin of enzymes from various organs. Therefore, bombesin-like peptides may be used as probes to investigate a large number of different cell types. In addition, these peptide has a relatively simple structure (10–27 amino acids) and can be synthesized and isolated with standard, well-known techniques.

During typical experiments, fluorescent markers for bombesin-like receptors emit optical signals, and thus may be monitored by eye or with the aid of external optical detectors. In this way, the fluorescent peptides obviate the need for secondary detection steps sometimes used for radiolabeled compounds or incubation with secondary labeled compounds. Detection of optical radiation is, in general, relatively simple and cost-effective compared to detection of radioactive particles (e.g., α-particles); conventional charge-coupled device (CCDs) or light-sensitive cameras can therefore be used without modification for this application.

In addition, because of their high optical emission rates and well-characterized emission cross sections, fluorescent markers attached to bombesin-like peptide can be used for real-time, quantified imaging of a number of dynamic biological phenomena, such as kinetics associated with receptor binding. The compounds can also be used for static processes, such as monitoring peptide distribution within a cell. Bombesin-like peptide receptors marked with fluorescent peptides may also be used in flow cytometry, confocal microscopy, fluorescence polarization spectroscopy, and any other techniques exploiting the optical detection of fluorescence or photoluminescence.

Other advantages and features of the invention will become apparent from the following detailed description, and from the claims.

Definitions

"Bombesin-like peptide": "Bombesin-like peptide refers to any peptide, that belong to the bombesin subfamily of peptides. For example, any protein with substantial DNA or peptide sequence homology and similar biological activity to bombesin, as determined by one of ordinary skill in the art, would be considered to qualify as a bombesin-like peptide. "Bombesin-like peptide" or "bombesin-like compound" includes fragments of bombesin, derivatives or analogs thereof. Some examples include, GRP, NMB, NMC, and [Dphe$^6$, Ala$^{11}$, Phe$^{13}$, Nle$^{14}$]Bbn(6–14) as described in the present application. Bombesin-like peptides may be peptides whose sequences differ from bombesin's wild-type sequence by only conservative amino acid substitutions. For example, one amino acid may be substituted for another with similar characteristics (e.g., valine for glycine, arginine for lysine, etc.) or by one or more non-conservative amino acid substitutions, deletions, or insertions which do not abolish the peptide's biological activity. Alternatively, the bombesin-like peptide may contain modified amino acids, such as norleucine of [Dphe$^6$, Ala$^{11}$, Phe$^{13}$, Nle$^{14}$]Bbn(6–14). Other useful modifications include those which increase bombesin's stability. The peptide may contain, for example, one or more non-peptide bonds (which replace a corresponding peptide bond) or D-amino acids in the peptide sequence. Additionally, the C-terminus carboxylic acid group may be modified to increase peptide stability. For example, as described above, the C-terminus may be amidated or otherwise derivatized to reduce the peptide susceptibility to degradation.

"Fluorescent peptide" or "compound": As referred to herein, "fluorescent peptide" or "compound" refers to a peptide-based compound that has been labeled with a light emitting moiety. The fluorescent peptide has the desirable characteristics of preserving the biological activity of the peptide-based compound, for example in receptor binding, and providing a detectable signal that can be measured using standard optical means.

"Light emitting molecule": "Light emitting molecule," as used herein, refers to a molecule capable of emitting light of any detectable wavelength that is not attached to a peptide of the present invention.

"Light emitting moiety": "Light emitting moiety" is used to refer to a light emitting molecule (e.g., a fluorescent dye) that has been attached by any of a variety of means, as described below, to peptide-based moiety. Attachment to the peptide-based moiety is carried out so that the biological activity of the peptide-based moiety is maintained. The light emitting moiety provides a detectable signal of a particular wavelength. In general, the signal provided by light emitting moieties may be detected by a variety of techniques including conventional microscopy methods, including fluorescence or confocal microscopy, atomic force microscopy, fluorescence polarization spectroscopy and fluorimetry. Particularly preferred light emitting moieties are described in more detail below.

"Peptide moiety": "Peptide moiety", as used herein, refers to any peptide composed of any sequence of natural (i.e., found in nature) and/or custom amino acids. By "custom amino acid" is meant any amino acid that can not be found in nature, but can be synthesized in a laboratory. Such amino acids are often chemically modified amino acids. It is well known that natural amino acids may also be synthesized. Particularly preferred peptide moieties of the present invention include bombesin-like peptides. Most particularly preferred are the bombesin-like peptides NMB, NMC, GRP, and -[Dphe$^6$, Ala$^{11}$, Phe$^{13}$, Nle$^{14}$]Bbn(6–14).

"Linker moiety" or "linker": A "linker moiety" or "linker" is any moiety of the compound located between the peptide and the label or at any other position which provides greater three dimensional separation between the label and the peptide. One particularly preferred linker moiety used in the present invention is based on γ-aminobutyric acid. Other moieties that may be used as linkers in the present invention include those derived from glycine, beta-alanine, aminopentanoic acid, aminohexanoic acid, aminohepanoic acid, aminooctanoic acid, aminononanoic acid, aminodecanoic acid, aminoundecanoic acid, and aminododecanoic acid. Each of these moieties include an amino and a carboxylic acid functionality and so may be incorporated into the compound using a peptide bond.

"Biologically active compound" or "biologically active peptide": "Biologically active compound" or "biologically active peptide", as used herein, refers to the fluorescently labeled peptide of the invention represented in the formula described below and in FIG. 1. Any biologically active compound of the present invention is substantially biologically active.

"Substantially biologically active": In all cases, by "substantially biologically active" is meant that the compound binds to a receptor having an affinity $IC_{50}$ or $K_i$ value for the compound which is no more than 100 times, preferably no more than 15 times, more preferably no more than 10 times and most preferably equal to or less than that of the corresponding unlabeled peptide. Most preferably, an affinity $IC_{50}$ or $K_i$ value for the compound is no more than 10 nM. Receptor affinity in this case can be determined using known methods, such as methods involving competitive binding of radioactively labeled peptides or by using known methods of fluorescence polarization or other known fluorescence technique for measuring the Kd for the receptor/peptide interaction.

"Low" or "no" biological activity or "biologically inactive": By "low" or "no" biological activity or "biologically inactive" is meant biological activities less than 0.25% of the biological activity of $R_2$—H in the presence of a receptor having affinity for bombesin-like peptides.

DETAILED DESCRIPTION OF THE INVENTION

Figure 1:
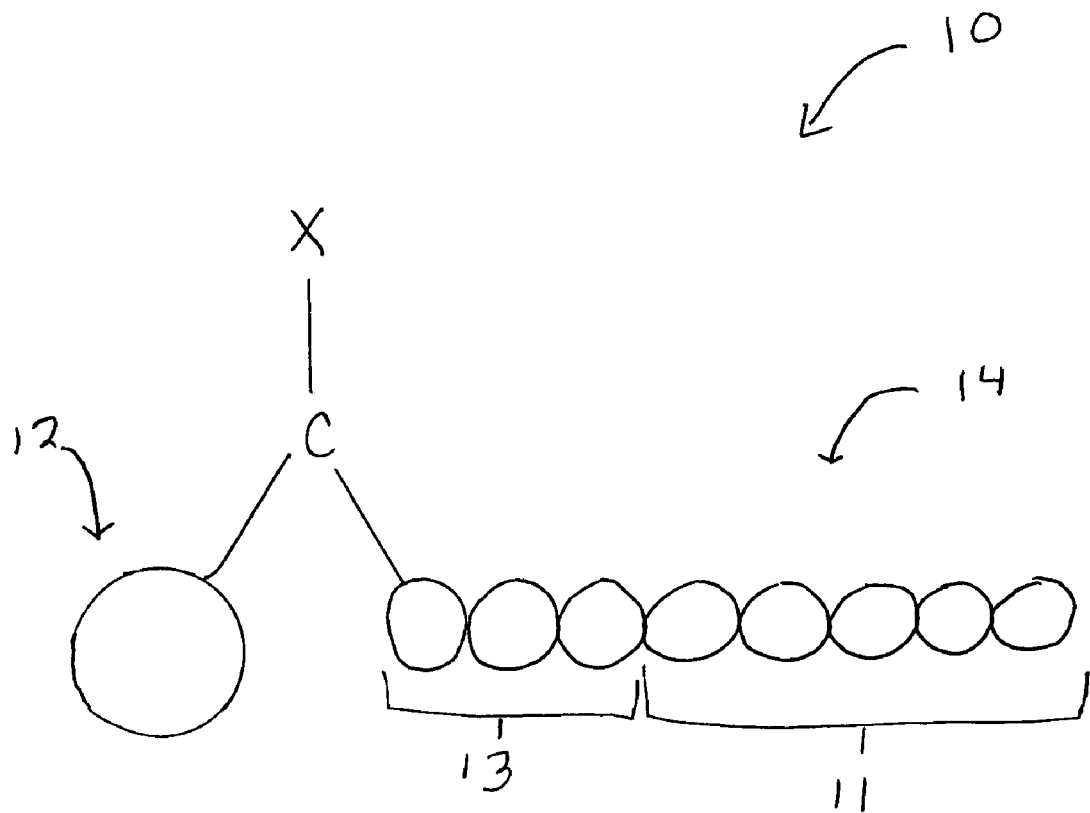
FIG. 1 is a schematic drawing of the chemical structure of fluorescently-labeled bombesin-like peptide according to the invention.
Figure 2:
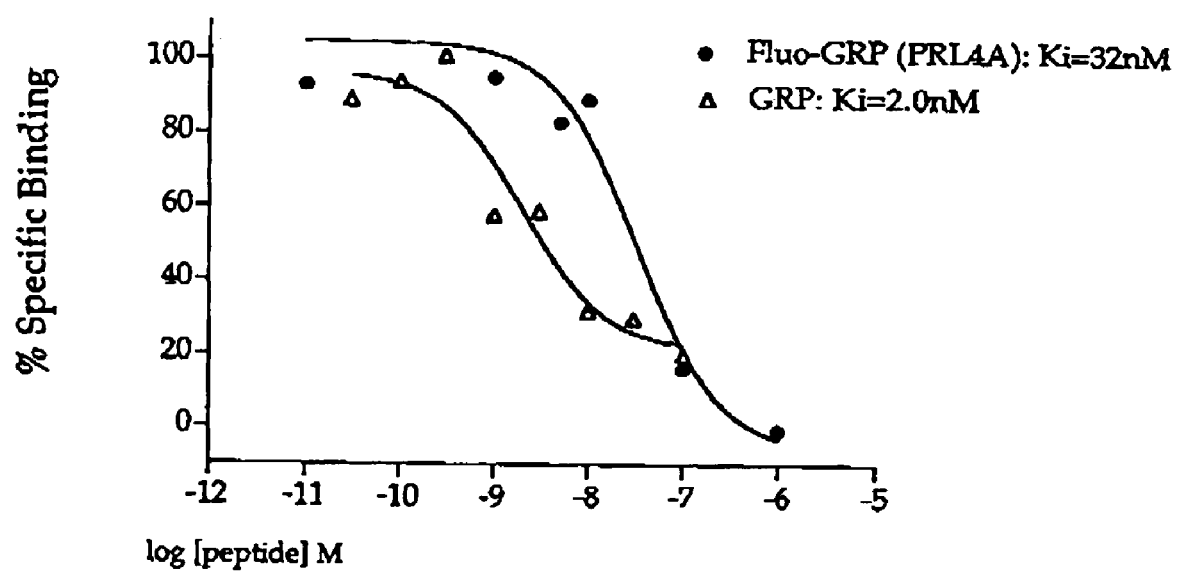
FIG. 2 is an IC50 curve showing displacement of $^{125}$I labeled bombesin from bombesin receptors BB1, BB2 and BB3 by increasing concentration of unlabeled and fluorescently labeled GRP.
Figure 3:
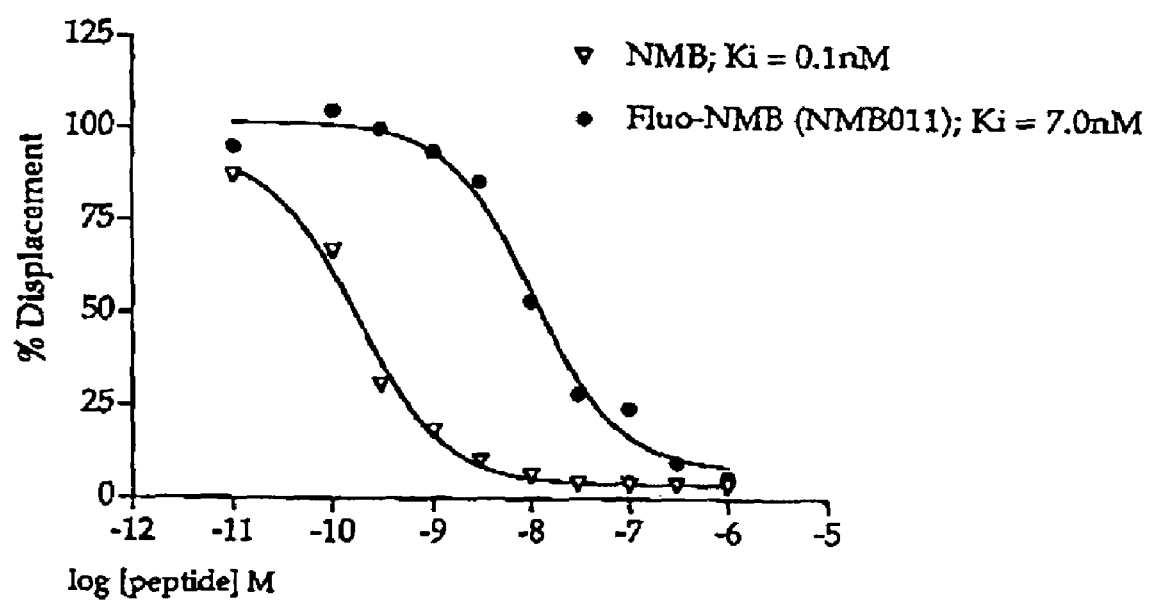
FIG. 3 is an IC50 curve showing displacement of $^{125}$I labeled NMB from BB1 (the NMB receptor) by increasing concentration of unlabeled and fluorescently labeled NMB.

The present invention provides biologically active labeled peptides that can be used in a variety of assays including labeling cellular receptors, cell sorting, flow cytometry and fluoroimmunoassays. In one preferred embodiment, (FIG. 1), a fluorescent peptide 10 according to the invention includes a light-emitting moiety 12, such as a fluorescent dye, linked via a (CX) bond to a peptide moiety 14. The peptide moiety 14 includes amino acid residues of a bombesin-like peptide, and fragments, derivatives or analogs thereof. The bombesin family of peptides share a common C-terminal amino acid sequence Trp-Ala-X-Gly-H's-X-Met-NH$_2$ 11 (SEQ ID NO:6) where full biological activity of bombesin and bombesin-like peptides resides. The N-terminal sequence 13 of bombesin and bombesin-like peptides has a modulatory role important for variation in selectivity of the peptides for different bombesin-like peptide receptors.

In order to retain substantial biological activity and affinity for bombesin-like peptide receptors, the peptide is attached to a fluorescent label via the (CX) linking moiety at an amino acid bound to the N-terminus (position 1). The N-terminus of position 1 is not essential for biological activity, i.e., it is not significantly involved in bombesin receptor binding (e.g., BB1). In this manner, the light-emitting moiety does not sterically hinder or otherwise significantly affect the region involved in receptor binding and the biological activity of the compound is thus maintained. For example, in a preferred embodiment, the peptide moiety NMB is attached to the N-terminal glycine (position 1) of the peptide via an αN-Gly1 bond to the light emitting moiety through a (C=O) bond. The light-emitting moiety may be covalently bonded to the (CX) linking group at any available position. The (CX) linking group represents the bond formed between the light-emitting moiety and the peptide upon reaction and this bond may include groups such as C=O, C=S, CH(OH), C=C=O, C=NH, CH$_2$, CH(OR), CH(NR), CH(R), $CR_3R_4$, and $C(OR_3)OR_4$ where R, $R_3$, and $R_4$ are alkyl moieties or substituted alkyl moieties.

Fluorescent peptides of this type have amino acids which are available for binding to bombesin-like peptide-recognizing receptors, thereby enabling the fluorescent peptide to be used for labeling purposes. Once the fluorescent peptide is bound to an available receptor, the attached light-emitting moiety retains optical properties similar to those of an unbound light-emitting molecule. In this way, the fluorescent peptide can bind to the corresponding receptor and emit light following absorption of an incident optical field, and thus serve as a marker for the bombesin-like peptide receptor. This allows the receptor to be "labeled" and permits investigation, for example, of peptide/receptor interactions. In particular, fluorescently labeled peptides participating in receptor/peptide interactions can be monitored to determine the location of receptors in cell or tissue samples, and additionally allow quantification of receptors, determination of the receptor affinity for various ligands, or the identification of various populations of cells.

In preferred embodiments of the present invention, a linker moiety may be used to provide greater three dimensional separation between the label and the peptide and to attach the peptide to the fluorescein label.

The invention provides labeled peptides that retain their biological activity. The combined practice of 1) attaching the label to a region of the peptide that is not essential for the biological activity of the; and 2) peptide providing a linker between the label and the peptide when necessary; facilitates maintenance of the biological activity of the peptide. The linker is chemically similar to an amino acid and is capable of forming peptide bonds with the bombesin-like peptide. A variety of linkers are known in the art that may be used in the present invention. For example, glycine, beta-alanine, aminopentanoic acid, aminohexanoic acid, aminohepanoic acid, aminooctanoic acid, aminononanoic acid, aminodecanoic acid, aminoundecanoic acid, aminododecanoic acid and β-(2-naphthyl)-L-alanine. In the present application, γ-aminobutyric acid is used as a linker in the compound fluoresceinyl-[Dphe[6], Ala[11], Phe[13], Nle[14]]Bbn(6–14) between the label and the N-terminal D-phenylalanine by forming a peptide bond between γ-aminobutyric acid and D-phenylalanine.

Bombesin-like peptides may be synthesized using techniques known in the art, extracted from natural systems, or obtained from commercial sources (e.g., American Peptide, Peninsula, Neosystems, Sigma, BASF). A list of the bombesin-like peptides referred to herein and their analogs that may be used to practice the invention may be obtained from American Peptide Co., Inc product catalogue. Typically, the peptide is either purchased or synthesized using conventional solid-phase synthetic techniques. Preferably, the peptide is substantially pure, meaning that it is at least 60% by weight free from the other compounds with which it is naturally associated.

Once the desired peptide is obtained, fluorescent peptides having high biological activities are made by attaching the light-emitting moiety to the first amino acid position of the bombesin-like peptide moiety. In general, this reaction is carried out by modifying a functional group on the peptide, most typically a thiol or amine group, so that this peptide moiety may be easily attached to the light-emitting moiety. Reactions for such modifications are described in, for example, "*Handbook of Fluorescent Probes and Research Chemicals—5th Edition*" (supra).

The conditions used to modify amine moieties of the desired peptide will depend on the class of amine (e.g., aromatic, aliphatic) and its basicity. Aliphatic amines, such as the α-amino acid groups of lysine and arginine, are moderately basic and reactive with acylating reagents. The concentrations of the free base form of the aliphatic amines below pH 8 is very low; thus, the kinetics of acylation reaction of amines by isothiocyanates, succinimidyl esters, and other reagents is strongly pH-dependent. Although amine acylation reactions should usually be carried out above pH 8.5, the acylation reagents degrade in the presence of water, with the rate increasing as the pH increases. Therefore, a pH of 8.5–9.5 is usually optimal.

In general, thiols or alcohols react with alkylating groups (R'—Z) to yield relatively stable ethers or thiol ethers (R'—S—R), e.g., (C—X) is the α-carbon of R', with the leaving group Z preferably being a halogen (e.g., Cl, Br, I) and the like. In particular, the most common reagents for derivatization of thiols are haloacetyl derivatives. Reaction of these reagents with thiols proceeds rapidly at or below room temperature in the physiological pH range.

In general, any dye, porphyrin, fluorophore, or other light-emitting molecule may be complexed with the bombesin-like peptide. In preferred embodiments, the light-emitting moiety is selected from the group including 4,4-difluoro-4-bora-3a,4a-diaza-s-indacene, fluorescein, FITC, Texas red, phycoerythrin, rhodamine, carboxytetra-methylrhodamine, indopyras dyes, Cascade blue, coumarins, NBD, Lucifer Yellow, propidium iodide, CY3, CY5, and CY9, dinitrophenol (DNP), lanthanide cryptates, lanthanide chelates, non-fluorescent dialdehydes (OPA, NDA, ADA, ATTOTAG reagents from Molecular Probes) which react with primary amines (N-term lysine in the presence of a nucleophile (i.e. CN⁻) to form fluorescent isoindoles, dansyl dyes, fluorescamine and dabcyl chloride, 5-((((2-iodoacetyl) amino)ethyl)amino)naphthalene-1-sulfonic acid, long lifetime dyes comprised of metal-ligand complexes (MLC) which consist of a metal center (Ru, Re, Os) and organic or inorganic ligands complexed to the metal such as such as $[Ru(bpy)_3]^{2+}$ and $[Ru(bpy)_2(dcbpy)]$, and the like and derivatives thereof. The synthesis and structures of several dyes which may be used are described in U.S. Pat. Nos. 5,248,782; 5,274,113; and, 5,187,288, the contents of which are incorporated herein by reference. Other light-emitting moieties used in labeling or other applications may be attached to the peptide. For example, suitable light-emitting moieties are described in "*Handbook of Fluorescent Probes and Research Chemicals—5th Edition*" by Richard P. Haugland 1994; and "Design and Application of Indicator Dyes", *Noninvasive Techniques in Cell Biology:* 1–20 by Richard P. Haugland et al., Wiley-Liss Inc. (1990), the contents of each of which is incorporated herein by reference. In general, reactive groups on the light-emitting moiety, such as unsaturated alkyl groups or acylating moieties, will react with the modified peptide to form a dye/peptide bond. The chemical structure of the light-emitting moiety may affect the synthetic route used to synthesize the fluorescent bombesin-like peptide analog. It may be necessary, for example, to modify the light-emitting moiety so that it includes a reactive group prior to exposing this moiety to the desired peptide. Such side groups may include indoacetamide, maleimide, isothiocyanate, succinimidyl ester, sulfonyl halide, aldehyde, glyoxal and hydrazine derivatives. Amino acids including alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine may be labeled according to the method described herein.

The chemistry used to synthesize the fluorescent peptide is not greatly dependent upon the exact structure of the bombesin-like peptide analog. Thus, the general procedure outlined below may be used for most bombesin-like peptides. Attachment of this peptide to a light-emitting moiety is described in detail in the Examples provided below.

Once synthesized, the resulting complex is purified, preferably using a column method such as high pressure liquid chromatography (HPLC), and then eluted. Collected fractions are then screened using analytical methods to determine if adequate biological activity is present. Fluorescent bombesin-like peptide analogs having adequate biological activities are selected by first exposing these analogs to bombesin-like peptide receptors; compounds binding effectively to these sites are then isolated from relatively inactive fluorescent peptides. In general, this selection process can be performed using standard techniques, such as column chromatography or other analytical techniques known in the art. The selection process is designed to allow maintenance of the compound's pharmacological binding, and thus allows only the dye/peptide compounds exhibiting substantial biological activities to be separated from relatively inactive compounds.

Figure 4:
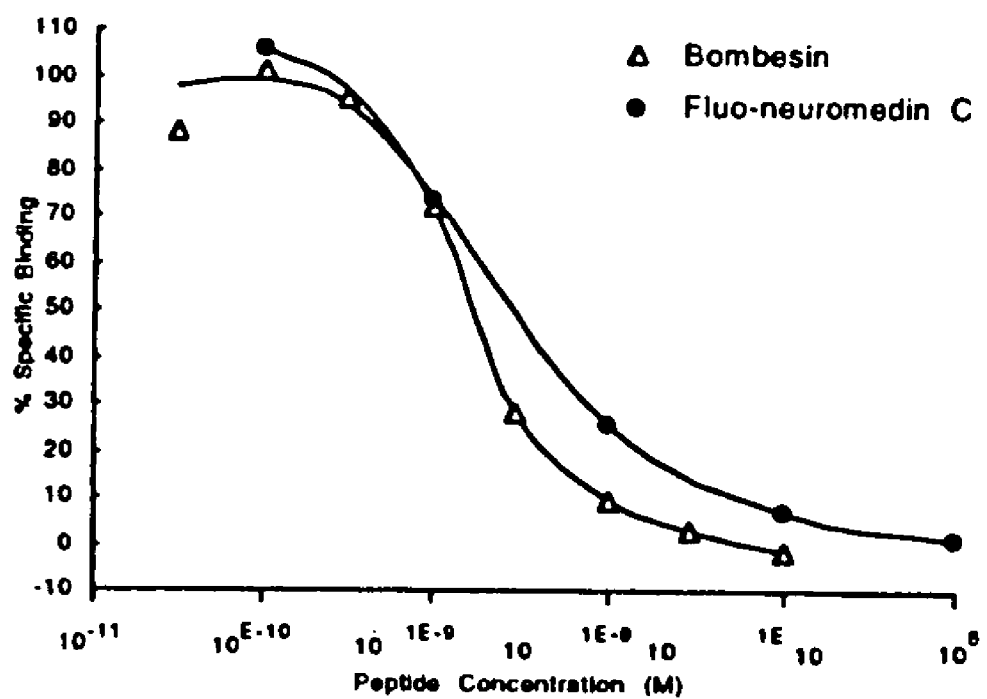
FIG. 4 is an IC50 curve showing displacement of $^{125}$I labeled bombesin from bombesin receptor BB2 by increasing concentration of unlabeled and fluorescently labeled NMC.
Figure 5:
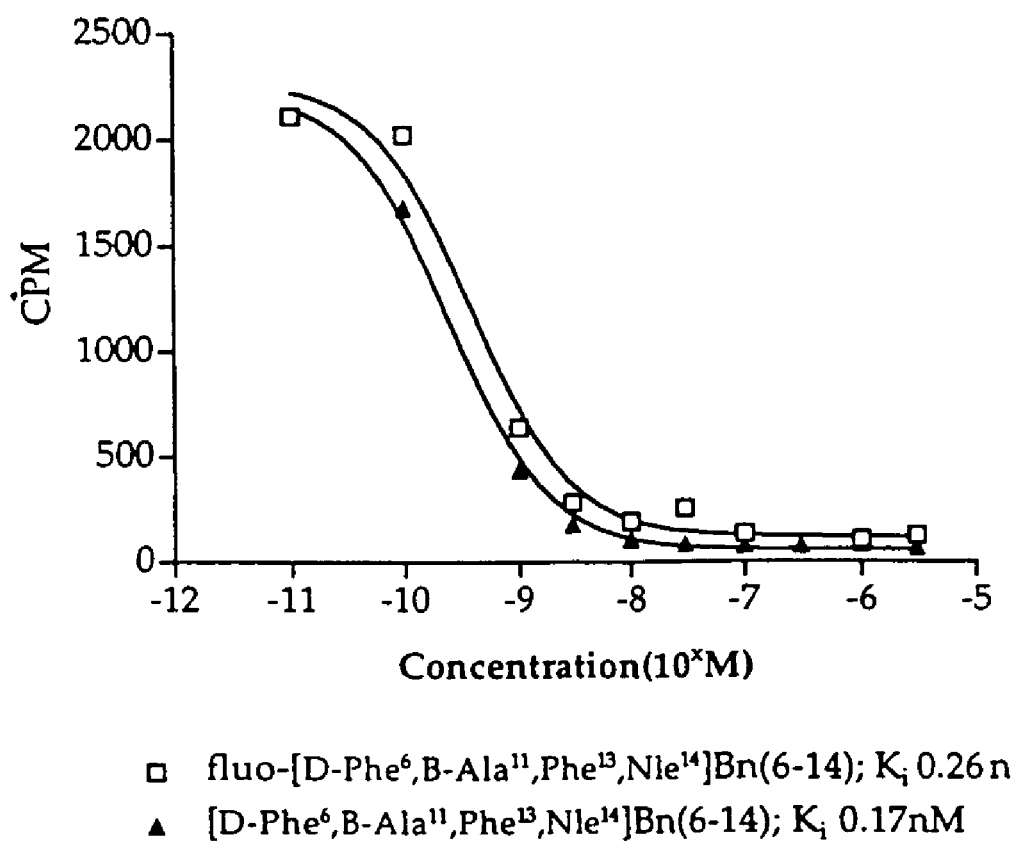
FIG. 5 is an IC50 curve showing displacement of $^{125}$I labeled GRP from the BB2 receptor by increasing concentration of unlabeled and fluorescently labeled GRP.
Figure 6:
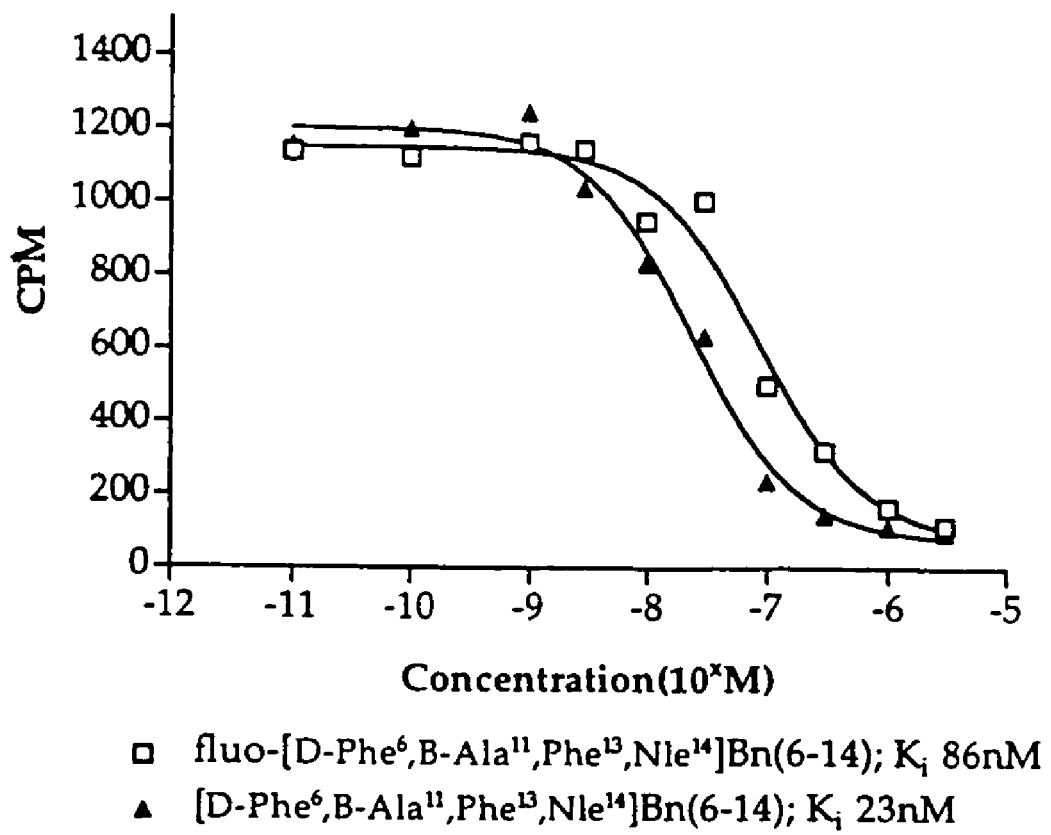
FIG. 6 is an IC50 curve showing displacement of $^{125}$I labeled -[Dphe$^6$, Ala$^{11}$, Phe$^{13}$, Nle$^{14}$]Bbn(6–14) from the BB3 receptor by increasing concentration of unlabeled and fluorescently labeled -[Dphe$^6$, Ala$^{11}$, Phe$^{13}$, Nle$^{14}$]Bbn (6–14).

Referring now to FIG. 4, a fluoresceinyl-NMC peptide with the amino aid sequence Gly-Asn-His-Trp-Ala-Val-Gly-His-Leu-Met-NH$_2$ (SEQ ID NO:4) was tested to determine its affinity for NMC receptor sites. The fluoresceinyl-NMC peptide compound absorbs light maximally at 494 nm and features an emission spectrum centered around 518 nm. The compound exhibits comparable, dose-dependent binding to the NMC-binding receptor, bombesin-receptor subtype 1 (BB1), when compared to native bombesin peptides, as determined by displacement of radiolabeled-bombesin peptides bound to receptors located rat cerebral cortex neurons in the brain. The concentrations at which 50% of the binding is inhibited (i.e., the IC50) is 3.2 nM for the fluorescein-labeled compound, as compared to 1.8 nM for the unlabeled bombesin. The IC$_{50}$ is related to the binding constant $K_i$ by the formula IC$_{50}$=$K_i$ (1+$F_L$/$K_d$), where $F_L$ is the concentration of the free labeled ligand and $K_d$ is the dissociation constant for the labeled ligand. The $K_i$ for this compound was 3.2 nM for the labeled compound versus 1.9 nM for the unlabeled compound. This demonstrates the high degree of retention of biological activity.

The $K_i$ data for other bombesin-like peptides for the perspective receptors is provided in Table 1 and FIGS. 2–6. All experimental results were obtained by displacing radio-labeled bombesin from the designated receptor, except for the results obtained for GRP which used radiolabeled GRP. Other receptors used in binding assays include the NMB receptor, the bombesin-receptor subtype 2 (BB2) and the bombesin receptor subtype 3 (BB3). As mentioned above, the biological activities of fluoresceinyl-NMC as well as fluoresceinyl-GRP compounds were determined in non-selective assay by binding to BB1, BB2 and BB3 expressed by rat brain neurons whereas the biological activities of fluoresceinyl-NMB and [Dphe$^6$, Ala$^{11}$, Phe$^{13}$, Nle$^{14}$]Bbn (6–14) compounds were determined by using recombinant cells expressing the BB1 (NMB receptor) or BB2 and BB3 receptors respectively.

TABLE 1

| Peptide | Receptor | Ki (nM) |
|---|---|---|
| Fluo*-NMC | BB1, BB2, BB3 | 3.2 |
| bombesin | BB1, BB2, BB3 | 1.8 |
| Fluo-GRP | BB1, BB2, BB3 | 32 |
| GRP | BB1, BB2, BB3 | 2.0 |
| Fluo-NMB | BB1 | 7.0 |
| NMB | BB1 | 0.1 |
| Fluo-[Dphe$^6$, Ala$^{11}$, Phe$^{13}$, Nle$^{14}$]Bbn(6–14) | BB2 | 0.26 |
| [Dphe$^6$, Ala$^{11}$, Phe$^{13}$, Nle$^{14}$]Bbn(6–14) | BB2 | 0.17 |
| Fluo-[Dphe$^6$, Ala$^{11}$, Phe$^{13}$, Nle$^{14}$]Bbn(6–14) | BB3 | 86 |
| [Dphe$^6$, Ala$^{11}$, Phe$^{13}$, Nle$^{14}$]Bbn(6–14) | BB3 | 23 |

*Represents that the peptide following is labeled.

In cases where it is not known which amino acid site may be complexed to form the fluorescent peptide of the invention, the peptide-fluorophore complexes may be screened to identify suitable complexes. The general synthetic method for identifying light-emitting biologically active compounds of the invention is as follows.

The bombesin-like peptide and the fluorophore of choice are incubated to form a mixture of compounds. Incubation is performed under conditions which permit optimal peptide labeling. Typically, a solution containing the peptide at a concentration of about $10^{-2}$–$10^{-4}$ M is mixed with the light-emitting moiety in a highly basic solution, i.e., pH 9.3–10.7 such as a carbonate buffer, in at least a 1:4 peptide:light-emitting moiety molar ratio. The solution is mixed at room temperature for a time of between about 24–48 hours, and is protected from light and shaken periodically. The resulting mixture includes biologically active and inactive whole peptides, cleaved fragments of peptides and singly and multiply labeled peptides.

After covalent bonding of the light-emitting moiety and the peptide occurs, unbound fluorophore is removed. In general, this step is performed using standard techniques such as column chromatography or other analytical techniques known in the art. In a typical example, unreacted amounts of the free fluorophore are removed using a G-50 column equilibrated with phosphate buffered saline (pH 7.4) and spun a 3000 rpm for a period of between 0.5 and 20 minutes. The resultant eluent contains a mixture of labeled biologically active and inactive peptides.

This solution is then collected and subjected to a high-stringency pharmacological binding assay. In this assay, only biologically active compounds are bound to tissue receptors; inactive compounds are washed away. The assay is typically performed on tissue sections, receptor-coated columns or membrane homogenates. In a typical example, an aliquot of the fluorescent peptide mixture is first dissolved in an aqueous solution (1:100) and incubated with an immobilized tissue sample containing high numbers of the peptide receptor, e.g., receptor transfected membrane homogenates. Alternatively, recombinant cells expressing a particular receptor may also be used as a membrane-bound receptor source.

The selection process is designed to separate compounds exhibiting substantial biological activity from those relatively inactive compounds. If necessary, during the assay, binding of the biologically active compounds may be rapidly observed visually, in a fluorometer or by using more sensitive techniques such as fluorescence polarization spectroscopy.

The receptor-bound compounds are then removed from the tissue surface or cell membrane and analyzed to identify the site at which the fluorophore is attached, i.e., the site allowing fluorophore attachment without interference with receptor binding. Biologically active compounds bound to membrane receptors are separated from the remaining inactive fluorescent peptides in solution, either by centrifugation of membrane homogenates (typically at 3000 rpm for about 5 minutes) or, in the case of tissue sections, by rapidly rinsing the sections in incubation buffer at 4° C. The membranes are then resuspended in binding buffer with the biologically active compound removed from the cell surfaces by incubation in a high salt/acid wash solution.

Once isolated, biologically active compounds are analyzed using known techniques, such as carboxypeptidase digestion and capillary electrophoresis, laser induced capillary zone electrophoresis, mass spectroscopy, and/or HPLC or amino acid sequencing, to identify the site of attachment between the light-emitting moiety and the peptide.

Fluorescent bombesin-like compounds selected to have high biological activity have a number of uses. For most applications, the fluorescent compound is first contacted with the sample of interest. The compound is then incubated with the cell or tissues of the sample for a select time period and allowed to interact with the bombesin-like peptide receptor. If necessary, excess, non-specifically bound compound may be washed away.

Once the peptide is bound to the desired receptor site, the labeled sample is imaged using standard techniques known in the art. Conventional microscopy methods, such as fluorescence or confocal microscopy, may be used to optically excite and then detect emission from the labeled receptors. Other imaging techniques which can be used with the fluorescent bombesin-like peptide compounds include atomic force microscopy, fluorescence polarization spectroscopy, and fluorimetry.

Using the above techniques, small-scale features in the cell which normally would be difficult or impossible to detect are observed. For example, this allows visualization of intracellular receptor sites. Moreover, labeled peptides participating in peptide-receptor interactions can be monitored to determine the location of receptors, to determine receptor affinity for various unknown ligands (drug screening), and to identify various populations of cells endowed with peptide receptors. Optical radiation emitted from the fluorescing moiety can be easily and rapidly detected, allowing the fluorescent peptides to be used to monitor real-time receptor/peptide interactions. In this way, the compounds permit study of kinetic processes in the cell. Other applications include receptor sorting using FACS (fluorescence-associated cell sorting) and measurement of serum peptide levels using FIA (fluorescent immunoassays) either in vivo or in vitro for research or diagnostic purposes. In general, techniques which may utilize the compounds of the invention include, without limitation, flow cytometry, cell sorting (for example, top isolate populations of cells bearing a receptor of interest), tumor marking, competitive binding assays for drug screening, fluorescent immunoassays, and other in vitro experimental techniques involving compound labeling according to techniques known in the art.

The following Examples are used to more particularly point out the synthesis, selection methods, and use of fluorescent bombesin-like peptide analogs having high biological activities.

EXAMPLE 1

Synthesis of Bombesin-Like Peptides

Peptides were synthesized using solid phase peptide synthesis methods either manually or automated (MPS396 peptides synthesizer, Advanced ChemTech). Coupling of amino acid residues was accomplished via Fmoc peptide synthesis chemistry (Fields, et al., 1990, IJPPR 35, 161). Syntheses were performed on Wang or on amide Rink resins, with side chain of amino acids fully protected.

Benzotriazol-1-yloxytris(dimethylamino)phosphonium hexafluorophosphate (BOP), (benzotriazol-1-yloxy)tripyrrolidinophosphonium hexafluorophosphate (PyBOP) or o-(benzotriazol-1-yl)-N,N,N',N'-tetramethyluronium tetrafluoroborate (TBTU) were used as activation agents depending on the chemistry and difficulty of the coupling reaction. All chemicals were purchased from Advanced ChemTech, Bachem and Calbiochem/NovaBiochem. Formation of each peptide bond between residues of the sequence was ensured by using a 3 to 6 fold excess of coupling reagents and by "double coupling"; meaning that the coupling reaction was repeated for each amino acid added to the growing peptide chain.

EXAMPLE 2

Fluorescein Labeling of Peptides

Bombesin-like peptides were labeled using an orthogonal protection scheme making it possible to deprotect the N-terminal amino group of the N-terminal amino acid of the peptide (for example, Val of GRP, Gly of NMB, Gly of NMC, and γ-aminobutyric acid of [Dphe$^6$, Ala$^{11}$, Phe$^{13}$, Nle$^{14}$]Bbn(6–14)(through use of the γ-aminobutyric acid linker)) while leaving remaining reactive groups in the peptide protected and the C-terminus of the peptide attached to the resin.

A 3-fold excess (estimated peptide in nM to fluorescein) of the carboxylic form of fluorescein was used and the reaction was allowed to proceed for 24 hours. The reaction was stopped by repeated washing (10×12 ml) with DMF followed by methanol (3×12 ml) and ethanol (2×12 ml). The resin was air dried prior to cleavage from the resin, as described in the procedure above.

After the synthesis the peptides were cleaved from the resin using the Reagent K as a cleavage mixture. Water (2.5%), TIS (2.5%) EDT (2.5%) were used as scavengers. The peptides were then precipitated with cold diethyl ether. The precipitates were centrifuged, washed three times with diethyl ether, dissolved in 20%–50% acetonitrile/water mixture and lyophilized. Analytical data of crude products were performed using analytical reverse phase HPLC and electrospray mass spectroscopy.

The crude peptides were purified by HPLC on a Vydac C18 or C4 column, 2.5×25 cm, using a linear gradient of 10–50% acetonitrile in water, with 0.06% trifluoroacetate (TFA) or with 0.1% triethanolamine acetate buffer pH7.8 (1%/min gradient, 10 ml/min flow rate). Monitoring by UV at 215 nm or 254 nm. Analytical HPLC was used to estimation or purity of fractions. The final products were obtained as lyophilized with at least 95% purity estimated by analytical HPLC (Vydac C18, 0.46×25 cm, linear gradient 10–60% acetonitrile in water, 0.1% TFA, 1%/min, 1 ml/min flow rate, detection by UV absorption at 215 nm and/or 254 nm. The pure peptides were identified by molecular mass analysis using a SCIEX API III mass spectrometer.

The fluorescence intensity of the labeled peptides were measured on Beacon Fluorescence Polarization System (Panavera) or Cytofluor 96 well plate reader at gain 85.2 nmols sample of peptide dissolved in 50 ul of DMSO, vortexing and aliquoted to final concentration of 1 uM with buffer EARLS (450 uL), pH 7.4. Intensity of fluorescence (Em. 450/50 nm-Ex 530/25 nm) was measure for four concentrations in the range of 10–100 nmolar. Linear regression was used for slope calculation. This value was used to calculate of percentage of fluorescence of fluorescein itself as a sensitivity of specific response.

EXAMPLE 3

Pharmacological Binding

Determination of IC50 for labeled peptides. Samples were prepared for IC50 determination by dissolving 2–10 nmols of the sample into a final volume of 0.5 mL. In order to fully dissolve the peptide, the sample was reconstituted in 20 uL DMSO, vortexing well to ensure that all powder was completely dissolved, and then adding 0.48 mL of double distilled water. The stock solution was aliquoted to avoid repeated freezing and thawing of peptide. Unused aliquots were stored at −20° C. (protected from light) for maximum 24 hr.

Receptor binding was carried out on tissues of rat cortex homogenate for GRP, recombinant cells expressing BB1 (NMB receptor) for NMB, or recombinant cells expressing BB2 and BB3 for [Dphe$^6$, Ala$^{11}$, Phe$^{13}$, Nle$^{14}$]Bbn(6–14). Tests were conducted at least in duplicate with three repeats recommended at 5–7 test concentrations (from $10^{-11}$–$10^{-6}$ M depending on the binding values).

Data for native and labeled peptides were analyzed by non-linear curve fitting. This included statistical evaluation of fit and calculation of IC50 and $K_i$ values.

Other embodiments are within the scope of the following claims.

What is claimed is:

1. A compound of the formula:

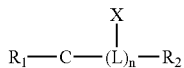

wherein $R_1$ is a light-emitting moiety and $R_2$ is a bombesin-like peptide, fragment, derivative or analog thereof, wherein $R_2$ is chosen from the group consisting of Val-Pro-Leu-Pro-Ala-Gly-Gly-Gly-Thr-Val-Leu-Thr-Lys-Met-Tyr-Pro-Arg-Gly-Asn-His-Trp-Ala-Val-Gly-His-Leu-Met (SEQ ID NO:2), Gly-Asn-Leu-Trp-Ala-Thr-Gly-His-Phe-Met (SEQ ID NO:3), and Dphe-Gly-Trp-Ala-Val-betaAla-His-Phe-Nle (SEQ ID NO:5), and L is a linker moiety, wherein n is 1 or 0, and (C—X) is selected from the group consisting of C=O, C=S, CH(OH), C=C=O, C=NH, $CH_2$, CH(OR), CH(NR), CH(R), $CR_3R_4$, and $C(OR_3)OR_4$ where R, $R_3$, and $R_4$ are alkyl moieties or substituted alkyl moieties, and wherein $(L)_n$—$R_2$ is linked to (C—X) at L or at an amino acid position selected such that the compound exhibits substantial biological activity in the presence of a receptor having affinity for bombesin-like peptides, wherein said compound exhibits substantial biological activity in the presence of a receptor having affinity for bombesin-like peptides.

2. The compound of claim 1, wherein n=0 and $R_2$ is directly attached to $R_1$.

3. The compound of claim 1, wherein n=0 and said amino acid position comprises the N-terminus of said bombesin-like peptide.

4. The compound of claim 2, wherein said N-terminus of said bombesin-like peptide is attached to (C—X) at αN-position.

5. The compound of claim 1, wherein said N-terminus amino acid residue is Val.

6. The compound of claim 1, wherein $R_1$ is bound, through C, to a region of said $R_2$ peptide which is not involved in said biological activity.

7. The compound of claim 1, wherein said $R_2$ peptide binds to a human receptor.

8. The compound of claim 1, wherein said light-emitting moiety is selected from the group consisting of 4,4-difluoro-4-bora-3a,4a-diaza-s-indacene, fluorescein, FITC, Texas red, phycoerythrin, rhodamine, carboxytetramethylrhodamine, indopyras dyes, Cascade blue, coumarins, NBD, Lucifer Yellow, propidium iodide, dinitrophenol (DNP), lanthanide cryptates, lanthanide chelates, non-fluorescent dialdehydes which react with primary amines to form fluorescent isoindoles, dansyl, fluorescamine and dabcyl chloride, 5-((((2-iodoacetyl) amino)ethyl)amino)naphthalene-1-sulfonic acid, long lifetime dyes comprised of metal-ligand complexes (MLC) and derivatives thereof.

9. The compound of claim 1, wherein (C—X) is selected from the group consisting of C=O and C=S.

10. The compound of claim 1, wherein said compound is a pharmaceutically acceptable salt or complex thereof.

11. A method for labeling a receptor having an affinity for a bombesin-like peptide by contacting said receptor with the compound of claim 1.

12. A method for generating a biologically active compound of claim 1, comprising:
reacting $R_1$ and $R_2$ in an aqueous solution to form a mixture comprising the compound of claim 1 and secondary compounds having biological activities less than 0.25% of the biological activity of $R_2$—H in the presence of a receptor having affinity for bombesin-like peptides;
contacting the mixture with a receptor for bombesin-like peptides; and
isolating from said mixture a light-emitting compound exhibiting substantial biological activity in the presence of said bombesin-like peptide receptor.

13. The method of claim 12, wherein said isolating step comprises:
releasing said light emitting compound from said bombesin-like peptide receptor; and
isolating said light-emitting compound.

14. The method of claim 13, wherein said step of isolating said light-emitting compound includes selection by high pressure liquid chromatography.

15. A method for imaging cell receptor sites comprising contacting candidate cell receptor sites with a compound of claim 1, and detecting said bound compound as an indication of said cell receptor sites.

16. A method of cell sorting comprising contacting a population of candidate cells with a compound of claim 1, and isolating cells bound to said compound.

17. A method of flow cytometry comprising contacting a population of cells with a compound of a claim 1 and detecting cells bearing receptors on their surfaces by detecting cells bound to said compound.

18. The compound of claim 1, wherein n=1 and $R_2$ is attached to $R_1$ via a linker moiety.

19. The compound of claim 1 wherein the linker moiety is selected from the group consisting of include g-aminobutyric acid, glycine, beta-alanine, aminopentanoic acid, aminohexanoic acid, aminohepanoic acid, aminooctanoic acid, aminononaoic acid, aminodecanoic acid, aminoundecanoic acid, and aminododecanoic acid.

20. The compound of claim 1 wherein $R_2$ is comprised of Gly-Asn-His-Trp-Ala-Val-Gly-His-Leu-Met (SEQ ID NO:4).

21. The compound of claim 1, wherein $R_2$ is comprised of (SEQ ID NO:5) and is attached to the linker γ-aminobutyric acid.

* * * * *